United States Patent [19]

Brinkerhoff et al.

[11] Patent Number: 4,747,531
[45] Date of Patent: May 31, 1988

[54] ANVIL AND DRIVER ASSEMBLY FOR A SURGICAL SKIN STAPLING INSTRUMENT

[75] Inventors: Ronald J. Brinkerhoff, Moscow, Ohio; Michael A. Murray, Bellevue, Ky.

[73] Assignee: Ethicon, Inc., Somerville, N.J.

[21] Appl. No.: 29,074

[22] Filed: Mar. 23, 1987

[51] Int. Cl.$^4$ ............................................. B25C 5/02
[52] U.S. Cl. ................................. 227/19; 128/334 R
[58] Field of Search ................... 227/19, 61, 82, 83, 227/92, 120, DIG. 1; 128/334 R, 335

[56] References Cited

U.S. PATENT DOCUMENTS

| | | | |
|---|---|---|---|
| 4,109,844 | 8/1978 | Becht | 227/19 |
| 4,256,251 | 3/1981 | Moshofsky | 227/19 |
| 4,411,378 | 10/1983 | Warman | 227/19 |
| 4,619,262 | 10/1986 | Taylor | 227/19 |

Primary Examiner—E. R. Kazenske
Assistant Examiner—James L. Wolfe
Attorney, Agent, or Firm—Gibson R. Yungblut; W. Brinton Yorks, Jr.; Paul A. Coletti

[57] ABSTRACT

An anvil and driver assembly for a surgical skin stapling instrument producing formed and implanted skin staples of more consistant and perfect configuration. The anvil provides an anvil surface which supports the crown of the staple during the forming operation. The driver has an inverted U-shaped notch formed therein which defines parallel side edges to bend the staple legs about the anvil and a transverse edge joining the side edges and adapted to contact the crown of the staple near the end of the forming operation. In the anvil and driver assembly of the present invention, the clearance between the parallel bending edges of the driver and the adjacent anvil edges is greater than the transverse dimension of the staple wire. The anvil surface of the anvil is concave and the crown contacting edge of the driver is so configured as to impart a temporary bow in the staple crown near the bottom of the driver stroke, which bow is of such dimension as to preclude plastic deformation of the crown. This produces a more generous bend and a slight over-bend at the junctures of the staple legs and the crown such that when the crown is released by the driver and returns to its rectilinear state, this action of the crown will compensate for the natural spring-back properties of the material from which the staple is made at the above noted junctures, consistantly producing the desired final formed configuration of the staple.

15 Claims, 6 Drawing Sheets

ANVIL AND DRIVER ASSEMBLY FOR A SURGICAL SKIN STAPLING INSTRUMENT

TECHNICAL FIELD

The invention relates to an improved anvil and driver assembly for a surgical skin stapling instrument and more particularly to an anvil and driver assembly so configured as to impart a concave bow, within the elastic limit, to the crown of the staple during the forming operation to slightly overbend the junctures of the staple legs and the staple crown such that when the crown is released by the driver and elastic spring back returns it to its rectilinear state, the bends at the aforementioned juncture are as desired.

BACKGROUND ART

In recent years surgeons have come more and more to the use of surgical staples (sometimes referred to as staple sutures), rather than conventional thread sutures, for the closing of wounds or incisions in the skin of a patient. This is true in part because the use of surgical staples is a far easier procedure. Of even greater importance, however, is the fact that the use of surgical staples is very much faster. Thus, the time required for suturing can be substantially reduced, thereby reducing the length of time the patient must be maintained under anesthesia.

Prior art workers have developed various types of surgical skin staplers. U.S. Pat. No. 3,873,016 teaches a pliers-like surgical stapler exemplary of those wherein the driver engages the forewardmost staple of a row thereof in a magazine and shifts the staple to an anvil and thereafter forms the staple about the anvil. U.S. Pat. Nos. 4,109,844 and 4,178,057 teach surgical stapling instruments of the type provided with an anvil plate having a coextensive, forwardly extending anvil provided with an anvil surface. A row of staples is mounted on the anvil plate and means are provided to constantly urge the row of staples forwardly so that the forwardmost staple of the row is located on the anvil plate. The driver thereafter is used to form the forwardmost staple about the anvil, but no part of the force required of the surgeon is used to shift a staple to the anvil. U.S. Pat. No. 4,411,376 teaches an improved form of anvil plate having forward extensions such that the legs of all of the staples on the anvil plate and anvil are supported except the forwardmost staple in position to be formed and implanted. U.S. Pat. No. 4,485,953 describes a surgical stapling instrument adapted to extract a staple from a separate cartridge thereof and to thereafter form and implant the staple in the skin of the patient.

The above description of surgical skin stapler types is representative only, and is not intended to be exhaustive. Most surgical skin staplers, however, are characterized by similar anvil-driver assemblies in that, during the forming and implanting operation, the anvil is located directly above the wound or incision. The anvil is characterized by a flat anvil surface located substantially parallel to the skin surface of the patient. The anvil surface supports the crown portion of the staple to be formed and implanted.

The typical driver of prior art anvil and driver assemblies has an inverted U-shaped notch formed therein. The U-shaped notch defines parallel bending surfaces adapted to bend the staple legs about the anvil and at the same time implant the staple legs in the skin of a patient. The upper end of the driver notch provides a transverse surface substantially perpendicular to the parallel bending surfaces and extending therebetween. This transverse surface comprises a staple crown-contacting surface which engages the staple crown at the bottom of the driver stroke. The space between the edges of the anvil and the parallel bending surfaces of the driver are such as to tightly accommodate the staple legs. This is true so that the sharpest possible bend is achieved at the juncture between the staple legs and the crown.

The above described interaction between the anvil and the driver has certain drawbacks. For example, the bends produced during the forming procedure at the junctures of the staple legs and the crown are severe and constitute substantially a coining operation. In addition, when the driver returns to its retracted position, the surgical staple has a tendency to be dragged with it. Furthermore, there sometimes is difficulty in slipping the anvil out from under the fully formed and implanted staple. A strong return spring must be used to return the driver to its normal retracted position, since at the completion of the forming and implanting step the staple legs are wedged between the parallel bending surfaces of the driver and the edges of the anvil. Finally, due to natural elastic springback of the wire from which the surgical staple is made, the staple legs tend to separate slightly after release from the driver and anvil so that an absolutely perfectly formed staple is difficult to achieve.

At the present time, the majority of surgical staples are made from metallic wire. Not all surgical staples are made of metallic wire, however. For example, some surgical staples are made of materials which will dissolve in the body environment over a period of time. The present invention will be described in terms of the use of metallic wire staples, but it is to be understood that the invention is applicable to the use of surgical staples made of any appropriate, resilient, permanently deformable material.

The present invention is based upon the discovery that if the anvil surface of the anvil and the staple crown contacting surface of the driver are so configured as to impart a slight concave bow to the crown portion of the staple during the forming and implanting procedure, and if the bow is of such size as to be within the elastic limit of the material from which the staple is made so that the staple crown is not plastically deformed, the junctures of the legs and crown can be slightly overbent so that when the staple crown is released by the driver, it can return to its rectilinear configuration and perfect square bends can be achieved at the junctures of the legs and the crown, producing consistently perfectly formed and implanted staples. In other words, the natural springback of the material from which the staple is made tends to bring the staple into perfect configuration, rather than to spread the staple legs away from a perfect configuration. Additional benefits are also derived from the present invention. For example, greater tolerance can be permitted between the parallel bending surfaces of the driver and the adjacent edges of the anvil. The staple does not have a tendency to be dragged with the driver as the driver is shifted to its normal retracted position and the anvil is more easily slipped from beneath the crown after forming and implanting. Less force is required to form the staple since more generous bends are formed at the juncture of the legs and the staple crown. Since the staple is not wedged between the parallel bending surfaces of the driver and the adjacent edges of the anvil, a return spring having a lesser force can be used to return the driver to its normal retracted position. The teachings of the present invention can be applied to any of the above described types of surgical stapling instruments.

It is known to provide non-surgical staple with a crown portion having a permanent concave bow therein. This is taught, for example, in U.S. Pat. No. 2,351,608. This permanent concave crown bow is provided so that when the staple is driven into a relatively hard workpiece such as wood by a hammer, the hammer blows are applied to the staple at two points substantially in line with the axes of the staple legs. This minimizes bending of the staple legs during the driving operation. The concave shape of the staple crown is permanent and bears no relationship to a forming operation.

U.S. Pat. No. 2,687,061 teaches the use of staples having permanent concave crown portions in a substantially conventional desk-top stapler. The concave crown portion of the staples cooperates with the staple pusher in the magazine in such a way as to reduce the likelihood of staples jamming in the magazine. Again, the concave crown of this reference has nothing to do with staple forming.

DISCLOSURE OF THE INVENTION

According to the invention there is provided an improved anvil and driver assembly for a surgical skin stapling instrument. The anvil provides an anvil surface which supports the crown of the staple during the forming operation. The driver has an inverted U-shaped notch formed therein which defines parallel side surfaces to bend the staple legs about the anvil and a transverse surface joining the side surfaces and adapted to contact the crown of the staple during the forming operation.

According to the present invention, the anvil surface is concave and the crown contacting surface of the driver is correspondingly convex so as to impart a concave bow to the surgical staple crown during the driver stroke of the forming and implanting procedure. The bow is of such magnitude as to be within the elastic limit of the wire or other material from which the staple is made so that the staple crown is not plastically deformed. The bow assures that the staple is slightly over-bent at the junctures of the staple legs and the crown. At the same time, the clearance between the parallel bending surfaces of the driver and the adjacent anvil edges is slightly greater than the transverse dimension of the wire from which the staple is made so that the bends at the junctures of the staple legs and the crown are more gentle bends than achieved by prior art structures, and require less bending force. As a result of the configuration of the anvil surface and the crown contacting surface of the driver, when the crown is released by the driver and springs back to its rectilinear state, the bend at the junctures of the legs of the staple crown will be more nearly square and the staple will be consistently formed into a more nearly perfect configuration.

DETAILED DESCRIPTION OF THE INVENTION

As indicated above, the teachings of the present invention are applicable to a number of different kinds of surgical skin stapling instruments. For purposes of an exemplary showing only, the present invention will initially be described in its application to a surgical skin stapling instrument of the type taught in U.S. Pat. No.

4,411,378. Such a surgical skin stapling instrument is shown in cross section in FIG. 1.

Figure 1:
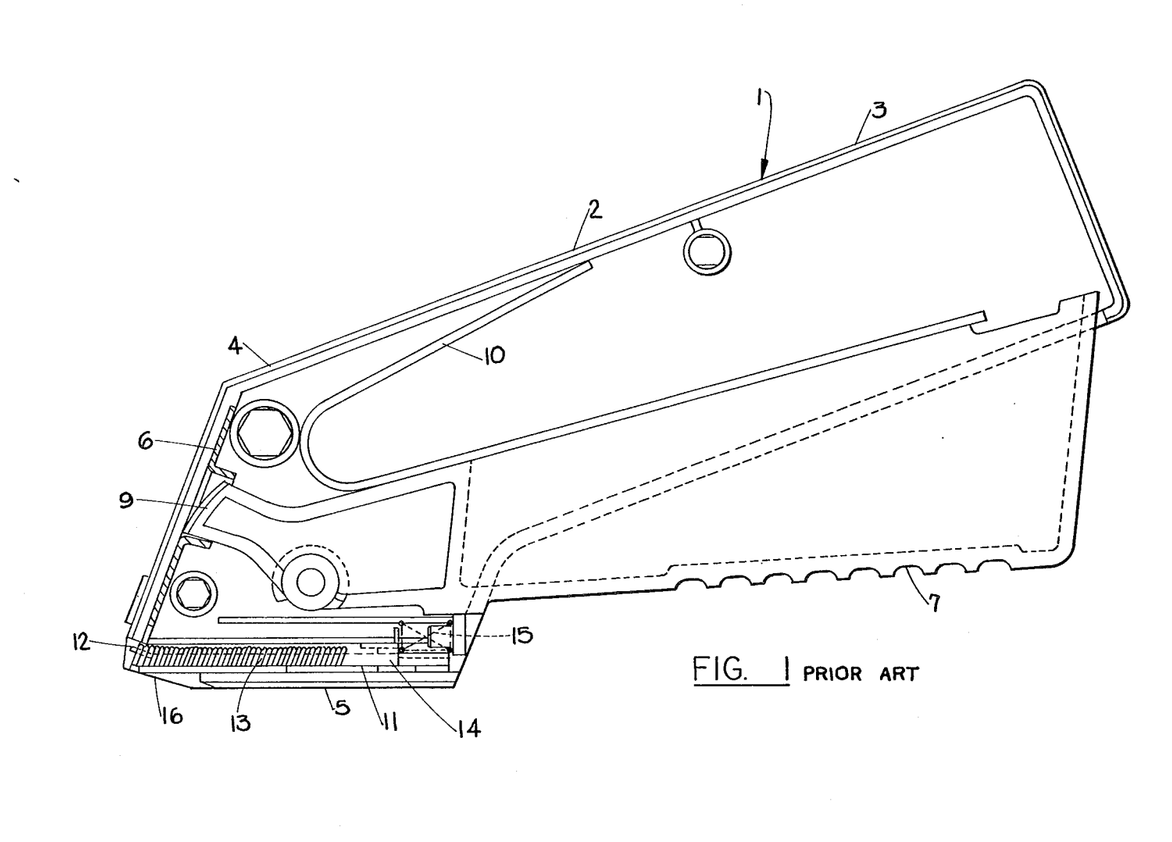
FIG. 1 is an elevational cross sectional view of an exemplary prior art surgical skin stapling instrument of the type to which the present invention is applicable.

FIG. 1 illustrates a disposable surgical stapling instrument for forming and implanting surgical staples in the skin of a patient. The surgical skin stapling instrument is generally indicated at 1 and comprises a body 2 having a rearward handle portion 3, a forward portion 4 and a magazine portion 5 located beneath the forward portion 4. A staple driver 6 is slidably mounted in the forward portion 4 of the instrument body 2. The staple driver 6 is shiftable between a first retracted or normal position (as shown) and a second extended or staple forming and implanting position. A trigger 7 is pivotally mounted within the body 2 as at 8. A portion of the trigger 7 is exposed beneath the body handle portion 3 for actuation by a surgeon. The forward end of the trigger 7 has a nose portion 9 in direct engagement with staple driver 6. The arrangement is such that when the exposed portion of trigger 7 is squeezed and caused to pivot into handle portion 3 of the body 2, the nose portion 9 of trigger 7 shifts the staple driver 6 from its first retracted position to its second extended position. A leaf spring 10 is located within the body 2 (primarily in the handle portion 3 thereof) above the trigger 7 to urge the trigger 7 to its normal unactuated position (as shown) and the staple driver to its normal or first retracted position.

The magazine portion 5 of the body 2 houses an anvil plate 11. The anvil plate 11 terminates at its forward end in a coextensive anvil 12 located beneath the driver 6. A row of surgical staples 13 is mounted on anvil plate 11 and is slidable therealong.

The magazine portion 5 of the instrument body 2 also houses a surgical staple feeder assembly. The feeder assembly comprises a feeder shoe 14 slidably mounted on the anvil plate 11 behind the row 13 of surgical staples and a simple compression spring 15 which constantly urges the feeder shoe against the row of staples and constantly urges the row of staples along the anvil plate 11 to place a forwardmost staple of the row on the anvil 12 to be formed by staple driver 6.

In operation, it is only necessary for the surgeon to locate the nose 16 of the instrument at the wound or incision site and thereafter squeeze trigger 7. The forwardmost staple of the row 13 will be formed and implanted in the patient's skin by driver 6. Upon release of trigger 7, the trigger 7 and driver 6 will return to their normal positions, permitting the next forwardmost staple of row to be located on anvil 12 by feeder shoe 14 and compression spring 15. At this point, the surgical stapling instrument 1 is again ready for use.

Figure 2:
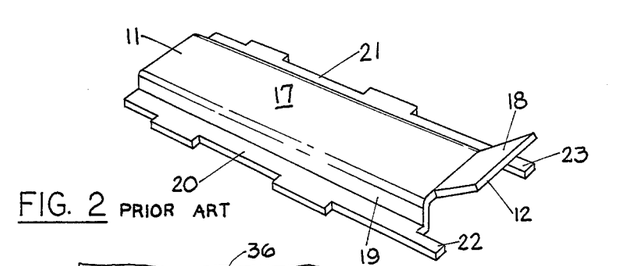
FIG. 2 is a perspective view of the anvil plate of the instrument of FIG. 1.

The anvil plate 11 of the instrument of FIG. 1 is most clearly illustrated in FIG. 2. The anvil plate 11 is preferably formed of an appropriate metal for use in a surgical environment, such as stainless steel or the like. The anvil plate 11 has a longitudinally extending raised central portion 17. At its forwardmost end, the raised central portion 17 terminates in anvil 12 which constitutes an integral one-piece part of the raised portion 17. The upper surface of anvil 12 constitutes anvil surface 18, which is coextensive with the upper surface of raised central portion 17.

The raised central portion 17 of anvil plate 11 has lateral edges which terminate in downwardly depending portions, one of which is shown at 19. The portion 19 and its equivalent portion on the other side of the anvil plate (not shown) terminate in laterally extending flanges 20 and 21. The laterally extending flanges 20 and 21 may be provided with forward extensions 22 and 23, respectively, the purpose of which will be apparent hereinafter.

Figures 3, 4:
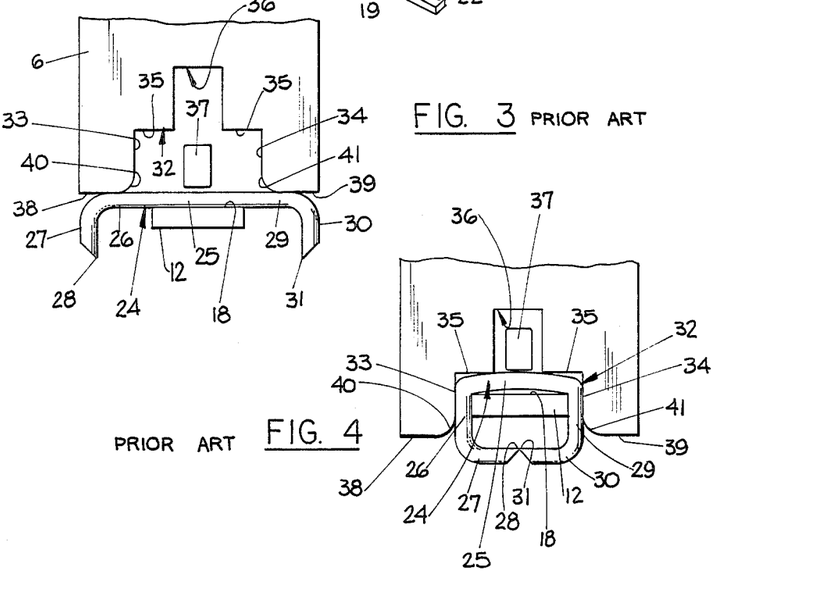
FIG. 3 is a simplified, fragmentary, elevational view of the anvil and driver of the instrument of FIG. 1, together with a staple, just prior to the forming and implanting step.
FIG. 4 is a simplified, fragmentary, elevational view similar to FIG. 3 and showing the anvil and driver of the instrument of FIG. 1, together with a staple, near the end of a forming operation.

Reference is made to FIG. 3 wherein a typical surgical staple, prior to forming and implanting, is generally indicated at 24. While not required, it is usual that the surgical staple 24 be made of wire of circular cross section. As is evident from FIG. 3, the staple in its initial, unformed condition comprises an elongated rectilinear portion terminating in downturned ends. That part of the elongated rectilinear portion supported by anvil surface 18 of anvil 12 comprises the crown 25 of the staple. That part of the rectilinear portion to the left of crown 25 constitutes a leg portion 26. The leg portion 26 terminates in a downturned leg portion 27 which, in turn, terminates in a sharp point or tip 28. Similarly, that portion of the rectilinear part of the unformed staple to the right of crown 25 (as viewed in FIG. 3) constitutes leg portion 29. Leg portion 29 terminates in downturned leg portion 30 which, itself, terminates in a point or tip 31.

As is evident in FIG. 1, the unformed staples are arranged in a tandem row straddling the upper raised portion 17 of anvil plate 11. The tips of the staples are supported by lateral flanges 20 and 21. The lateral flange extensions 22 and 23 assure that all of the staple legs are supported, except for those of the forwardmost staple of row 13, as is clearly shown in FIG. 1.

FIG. 3 also illustrates, in fragmentary form, the driver 6 of FIG. 1. The driver 6, at its lower end, has an inverted U-shaped notch (generally indicated at 32), formed therein. The U-shaped notch 32 defines a pair of vertical side edges 33 and 34 and a joining horizontal edge 35. The horizontal edge 35 may be interrupted by an additional notch, generally indicated at 36. The notch 36 may accommodate an element in the form of a lug or spring finger 37 mounted on the inside surface of the forward portion 4 of instrument body 2. The purpose of lug or spring finger 37 will be described hereinafter.

To complete the structure of driver 6, it will be noted that adjacent the vertical edges 33 and 34, the driver is provided with horizontal edges 38 and 39, respectively. At the juncture of vertical edge 33 and horizontal edge 38 there is a gently curved edge 40. Similarly, at the juncture of vertical edge 34 and horizontal edge 39 there is a gently curved edge 41.

FIG. 3 illustrates driver 6 at that point in its downward stroke (from its normal retracted position to its extended forming position) wherein it first contacts surgical staple 24. It will be noted that the lower horizontal edges 38 and 39 first contact leg portions 26 and 29 of staple 24 beyond the side edges of anvil 12. It will be apparent that as the driver 6 shifts further downwardly, leg portions 26 and 29 will begin to bend at the edges of anvil 12 (i.e. at their juncture with the crown portion 25 of staple 24). As leg portions 26 and 29 shift downwardly and inwardly toward each other, they will be contacted by the gentle curved edges 40 and 41 of driver 6, and ultimately by vertical edges 33 and 34 thereof.

FIG. 4 illustrates the driver near its extendedmost position. It will be noted that lug or spring finger 37 limits the amount of upward bowing of staple crown portion 25 during the bending operation. When the driver has reached its extendedmost position, its horizontal joining edge 35 will press staple crown portion 24 against anvil surface 18. It will further be noted from FIG. 4 that the clearances provided between the edges of anvil 12 and the vertical driver edges 33 and 34 are just sufficient to tightly engage staple leg portions 26 and 29 therebetween, in an attempt to achieve the squarest bends possible at the junctures of staple leg portions 26 and 29 and staple crown portion 25. When the staple is perfectly formed, the staple assumes a rectangular configuration with the leg points 28 and 31 aligned and substantially contiguous.

At the end of the forming operation, the driver will reverse its direction of travel and shift upwardly (as viewed in FIGS. 3 and 4) to its normal, retracted position (shown in FIG. 1) under the influence of leaf spring 10. Due to friction between the formed staple legs and the vertical driver edges 33 and 34, there is a tendency of staple 24 to drag upwardly with the driver. The amount by which the staple can shift upwardly with the driver is limited by the lug or spring finger 37. Once the driver 6 has attained its normal, retracted position, it is necessary to shift the skin stapling instrument 1 rearwardly of the staple to disengage anvil 12 therefrom. This is sometimes difficult because the staple is tightly formed about anvil 12.

Figure 5A:
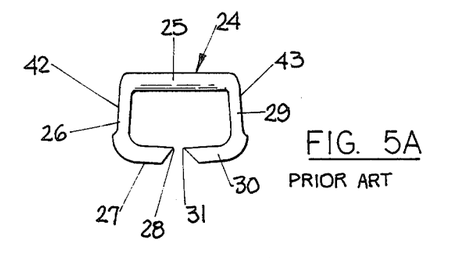
FIG. 5A illustrates the surgical staple of FIGS. 3 and 4 in its fully formed condition after release from the driver and anvil.
Figure 5B:
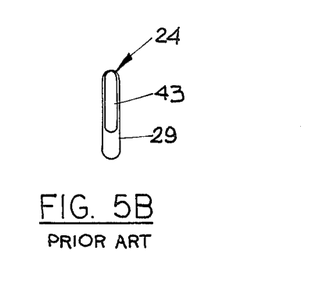
FIG. 5B is a side elevation of the staple of FIG. 5A, as seen from the right thereof.

Once the staple is free of driver 6, the natural spring back tendency of the wire or other material from which staple 24 is made tends to cause the staple leg tips 28 and 31 to separate slightly so that they are no longer in alignment and no longer nearly contiguous (see FIG. 5A). Leg portions 26 and 29 are no longer substantially parallel and leg portions 27 and 30 are no longer substantially coaxial. Thus, the desired perfect shape of the formed staple is very difficult to achieve. The bends at the junctures of leg portions 26 and 29 and crown portion 25 are severe and constitute substantially a coining operation, as is indicated in exaggerated form in FIG. 5A at 42 and 43, and in FIG. 5B at 43.

The general configuration of the driver 6 and the anvil 12, as shown in FIGS. 3 and 4, is typical of the configurations found in most prior art surgical skin stapling instruments. The fully formed staple of FIG. 5A, in slightly less than perfect shape, is again typical of the formed staples of most prior art instruments.

Figure 6:
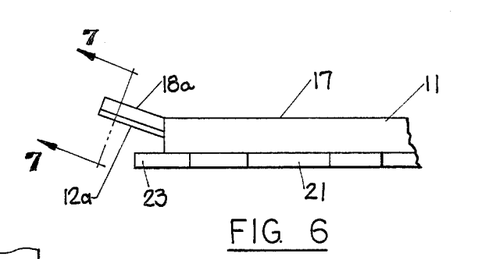
FIG. 6 is a fragmentary side elevational view of an anvil plate, similar to that of FIG. 2 and provided with an anvil of the present invention.
Figure 7:
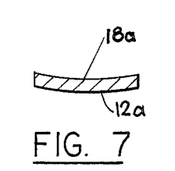
FIG. 7 is a cross sectional view taken along section line 7—7 of FIG. 6.

FIGS. 6 and 7 illustrate an anvil plate according to the present invention. The anvil plate is similar to that of FIG. 12, and like parts have been given like index numerals. The only difference between anvil plate 11 of FIG. 6 and anvil plate 11 of FIG. 2 lies in the coextensive anvil 12a and its anvil surface 18a. As can be most clearly seen in FIG. 7, the anvil surface 18a is concave.

Figure 8:
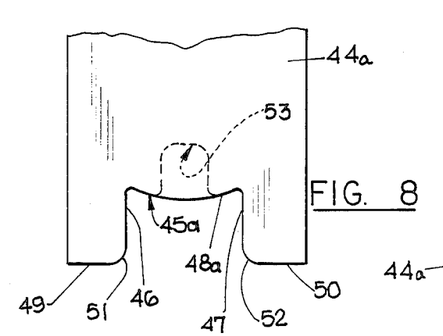
FIG. 8 is a fragmentary elevational view of a driver similar to that shown in FIGS. 3 and 4, but configured in accordance with the teachings of the present invention.

In FIG. 8, a driver 44a is illustrated, for use with the anvil plate 11 and its anvil surface 18a. The driver 44a has a notch, generally indicated at 45a, formed in its lower end, as viewed in FIG. 8. The notch 45a provides a pair of parallel leg bending edges 46 and 47, equivalent to the leg bending edges 33 and 34 of driver 6 of FIG. 3. The upper ends of leg bending edges 46 and 47 are joined by a transverse crown contacting edge 48a, equivalent to the crown contacting edge 35 of FIG. 3. The driver 44a is also provided with substantially horizontal edges 49 and 50, equivalent to horizontal edges 38 and 39 of FIG. 3. Between the vertical edge 46 and the horizontal edge 49 there is a rounded edge 51. Similarly, between the vertical edge 47 and the horizontal edge 50, there is a rounded edge 52. The rounded edges 51 and 52 are equivalent to the rounded edges 40 and 41 of FIG. 3. Finally, if the instrument in which the driver 44a is to be used is provided with a lug or spring finger equivalent to lug or spring finger 37 of FIGS. 3 and 4, the upper crown engaging edge can be additionally notched as at 53. Additional notch 53 serves the same purpose as the additional notch 36 of FIG. 3. It will be noted from FIG. 8 that the crown contacting edge 48a is convex and is arcuate in configuration and substantially corresponds to the arcuate concave anvil surface 18a. This is the only real difference between the driver 44a of FIG. 8 and the driver 6 of FIG. 3.

Figure 9:
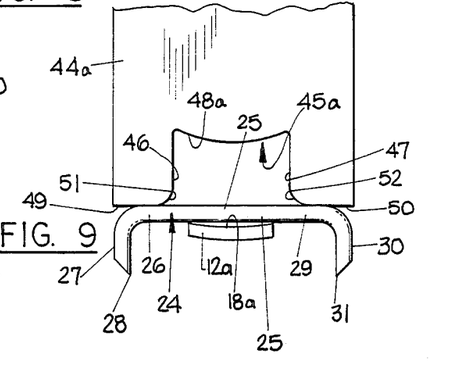
FIG. 9 is a fragmentary elevational view, similar to FIG. 3, and illustrating the anvil of FIGS. 6 and 7 and the driver of FIG. 8, together with a surgical staple, just prior to formation thereof.
Figure 10:
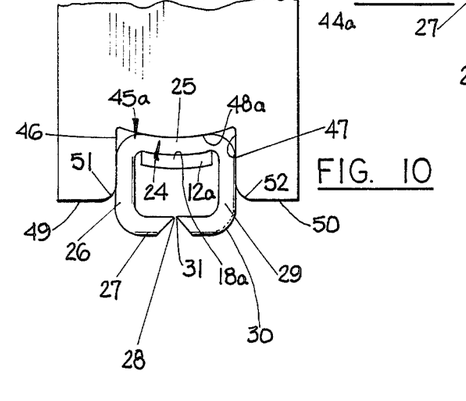
FIG. 10 is a fragmentary elevational view similar to FIG. 9 and illustrating the parts after the staple has been fully formed.
Figure 11:
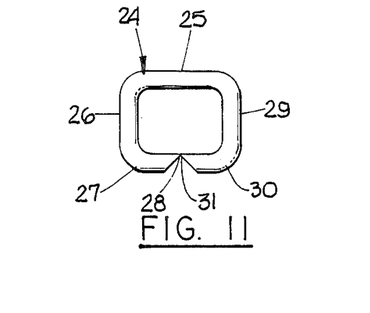
FIG. 11 illustrates the fully formed staple of FIGS. 9 and 10 after release by the driver and removal from the anvil.

FIGS. 9, 10 and 11 illustrate the manner in which driver 44a of FIG. 3 and anvil surface 18a of FIG. 7 cooperate. FIG. 9 is similar to FIG. 3 and shows a forwardmost staple mounted and supported by anvil surface 18a. The surgical staple illustrated in FIG. 9 is identical to the staple illustrated in FIG. 3, and like parts have been given like index numerals.

In FIG. 9, the driver 44a has shifted from its normal retracted position toward its forming position and is shown at its position of first contact with staple 24. It will be evident from FIG. 9 that the horizontal edges 49 and 50 first engage staple leg portions 26 and 29. As is apparent from a comparison of FIGS. 9 and 10, further downward progress of driver 44a will cause the leg portions 26 and 29 to thereafter be contacted by rounded driver edges 51 and 52, followed by vertical leg bending edges 46 and 47. FIG. 10 illustrates the driver 44a at the bottom of its stroke. Several things are to be noted in FIG. 10. First of all, the convex crown-contacting surface 48a of driver 44 has caused the crown 25 to conform to the concave bow of anvil surface 18a. The concave bow in crown 25 has, however, not exceeded the elastic limit of the wire from which staple 24 is made and therefore, crown 25 has not been plastically deformed. It will be noted that the bends at the juncture of crown 25 and leg portions 26 and 29 are more generous and that the clearances between the edges of anvil 12 and the adjacent vertical leg bending driver edges 46 and 47 is slightly greater than the transverse dimension of the staple wire. Finally, it will be noted that the staple points 28 and 31 are aligned and substantially contiguous.

When driver 44a is withdrawn to its normal retracted position, the bends at the junctures of leg portions 26 and 29 and crown portion 25 tend to open slightly due to natural spring-back. At the same time, however, crown 25 of staple 24 will return to its rectilinear condition. This is true because, as indicated above, the bow formed in the crown when the driver is at the bottom of its stroke does not create plastic deformation of the crown. When the crown 25 returns to its rectilinear condition, the points 28 and 31 of the legs maintain an aligned, nearly contiguous position. Return of crown 25 to its rectilinear condition compensates for the natural spring-back at the bends at the junctures of crown 25 and leg portions 26 and 29. FIG. 11 illustrates the staple once driver 44a has been retracted and the anvil 12a has been withdrawn therefrom. FIG. 11 shows a substantially perfectly formed surgical staple, a result consistently achieved with the structures of FIGS. 6–10.

Since the bow imparted to crown 25 in FIG. 10 does not exceed the elastic limit, so that plastic deformation of the crown does not take place, the natural spring-back tendency of the staple wire brings the staple into a more nearly perfect form, rather than away from a perfect form, as in the case of prior art instruments as illustrated in FIGS. 3–5B. With more generous bends formed at the junctures of leg portions 26 and 29 and crown 25, less force is required by the surgeon to form the staple. With greater clearance between the vertical leg bending driver surfaces 46 and 47 and the adjacent edges of anvil 12a, and with return of the staple crown 25 to its initial rectilinear state, there is less tendency for the staple to be dragged upwardly upon withdrawal of driver 44. As a result, a return spring 10 (see FIG. 1) of less force is required. Finally, as the crown portion 25 returns from its bowed state to its rectilinear state, it will elongate slightly, making withdrawal of the anvil 12a from beneath the crown 25 easier. The more generous bending of the staple at the juncture of its leg portions 26 and 29 and the crown 25 is not of the nature of a coining operation.

Figure 12:
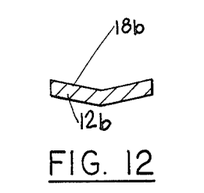
FIG. 12 is a cross sectional view similar to FIG. 7 and illustrating another embodiment of the anvil of the present invention.

As used herein and in the claims, the term "concave" as applied to the anvil surface is not limited to an arcuate concavity. Any appropriate, depressed center configuration can be used. FIG. 12, for example, is a cross sectional view similar to FIG. 7. In FIG. 12, the anvil 12b has a concave anvil surface 18b having a V-shaped configuration.

Figure 13:
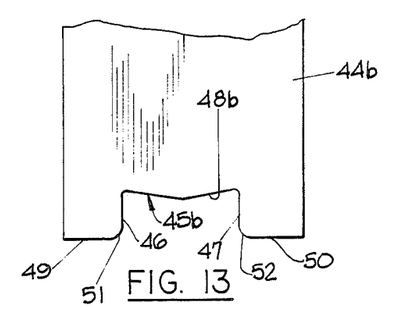
FIG. 13 is a fragmentary elevational view of a driver to be used with the anvil of FIG. 12.

FIG. 13 is a fragmentary elevational view of a driver 44b to be used with the anvil 12b. FIG. 13 is similar to FIG. 8, and like parts have been given like index numerals. The only difference between the driver 44b of FIG. 13 and the driver 44a of FIG. 8 lies in the fact that the convex crown-contacting edge 48b of FIG. 13 has a convex V-shape corresponding to the anvil surface 18b of FIG. 12. Thus the term "convex", as used herein in association with the driver, is not limited to arcuate convexity. The crown-contacting edge 48b may be provided with an additional notch (not shown) equivalent to the notch 53 of FIG. 8, if desired.

Figure 14:
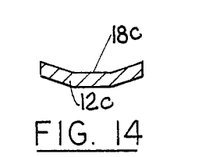
FIG. 14 is a fragmentary cross sectional view similar to FIG. 7 and illustrating yet another embodiment of the anvil of the present invention.

FIG. 14 is a cross sectional view similar to FIG. 7 and shows an anvil 12c having a concave anvil surface 18c which is faceted, having a rectilinear depressed central surface flanked by upwardly and outwardly sloping lateral surfaces. Thus, the concave anvil surface may be made up of a number of adjacent surfaces.

Figure 15:
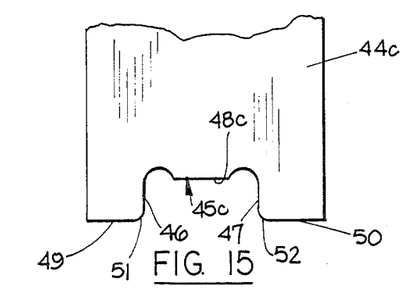
FIG. 15 is a fragmentary elevational view of a driver to be used with the anvil of FIG. 14.

FIG. 15 is similar to FIG. 8 and illustrates a driver 44c to be used with the anvil 12c of FIG. 14. Again, like parts have been given like index numerals. In this instance, the crown-engaging convex edge 48c comprises a central rectilinear surface flanked by a pair of arcuate surfaces. Again, the central recilinear surface can be interrupted by an additional notch (not shown) similar to the notch 53 of FIG. 8, if desired. FIGS. 14 and 15 illustrate the fact that the shape of the crown-contacting edge of the driver need not match the shape of the anvil surface.

The combination of anvil 12b and driver 44b and the combination of anvil 12c and driver 44c operate in substantially the same manner described with respect to FIGS. 9 and 10 and demonstrate the same results and advantages.

Figure 16:
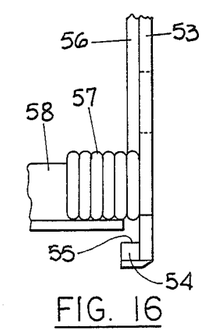
FIG. 16 is a fragmentary side elevational view of another type of anvil in accordance with the present invention, including a driver.
Figure 17:
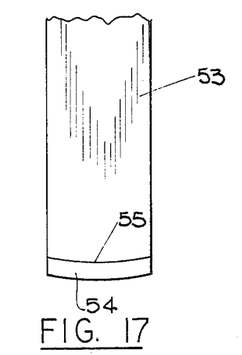
FIG. 17 is an elevational view of the anvil of FIG. 16.

FIGS. 16 and 17 illustrate another form an anvil. FIG. 17 is an elevational view of the rearward side of an anvil plate 53, normally mounted at the forward end of a surgical stapling instrument. The anvil plate has a rearwardly extending anvil 54 providing an anvil surface 55. As is most clearly seen in FIG. 16, a driver 56 is mounted adjacent the rearward face of anvil plate 53. The driver 56 is capable of being shifted from its normal retracted position shown in FIG. 16 toward anvil 54 to a staple forming position. A row of staples 57 is mounted on a staple guide 58. Means (not shown) are provided to constantly urge the row of staples 57 toward anvil plate 53. The forwardmost staple of the row is maintained off the forward end of staple guide 58 between the row of staples 57 and the rearward surface of anvil plate 53. When the driver 56 is shifted downwardly (as seen in FIG. 16), it strips the forwardmost staple from the row and shifts the forwardmost staple downwardly to anvil surface 55, about which the staple is formed by the driver 56. Once the staple has been formed and the driver retracted, the instrument is moved slightly forward to disengage the anvil 54 from beneath the staple crown.

It will be apparent from FIG. 17 that anvil 54 is similar to anvil 12a of FIG. 7, having an anvil surface 55 identical to anvil surface 18a of FIG. 7. The driver 56 will be provided with a notch (not shown) configured substantially identically to the notch 45a in driver 44a of FIG. 8. As a result, the forming step of the structure of FIG. 16 will be substantially identical to that described with respect to FIGS. 9–11.

Figure 18:
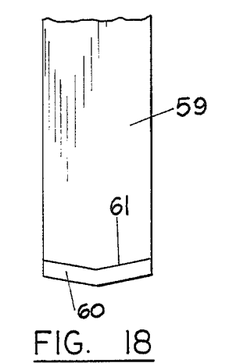
FIGS. 18 and 19 are elevational views, similar to FIG. 17, illustrating modifications of the anvil.

FIG. 18 illustrates an anvil plate 59 similar to anvil plate 53 of FIG. 17. In this instance, however, anvil plate 59 has an anvil 60 with an anvil surface 61 similar to anvil 12b and anvil surface 18b of FIG. 12. The anvil plate 59 will be used with a driver having a notch and crown contacting edge substantially identical to notch 45b and crown contacting edge 48b of FIG. 13.

Figure 19:
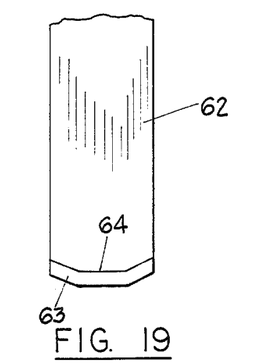

FIG. 19 illustrates an anvil plate 62 having an anvil 63 with an anvil surface 64. The anvil 63 and anvil surface 64 are similar to anvil 12c and anvil surface 18c of FIG. 14. Anvil plate 62 would be used with a driver having a notch and crown contacting edge equivalent to the notch 45c and crown contacting edge 48c of driver 44c of FIG. 15. It will be understood that the operation of anvil plate 59 of FIG. 18 and anvil plate 62 of FIG. 19, together with their respective drivers, will be otherwise substantially similar to that described with respect to FIGS. 9–11.

Figure 20:
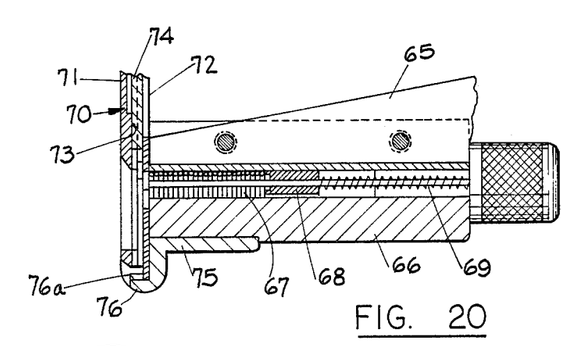
FIG. 20 is a fragmentary cross sectional view of another type of surgical skin stapling instrument provided with an anvil in accordance with the teachings of the present invention.
Figure 21:
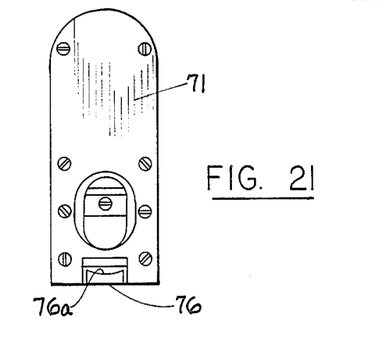
FIG. 21 is a front elevational view of the structure of FIG. 20, as viewed from the left of FIG. 20.

FIGS. 20 and 21 illustrate the teachings of the present invention applied to a surgical stapling instrument of the type taught in U.S. Pat. No. 3,873,016.

U.S. Pat. No. 3,873,016 teaches a pliers-like surgical stapling instrument, the lower jaw of which is illustrated in FIGS. 20 and 21. The lower jaw 65 supports a staple feed housing 66 in which a row of staples 67 is slidably mounted. The row of staples is constantly urged forwardly by a pusher head 68, and a compression spring 69.

To the forward end of lower jaw 65 and staple feed housing 66 there is affixed a vertical staple guide, generally indicated at 70. The staple guide comprises a front plate 71 and a rear plate 72 forming a slideway 73 therebetween. A ram or driver 74 is mounted in the slideway 73 and is operatively connected to the upper jaw (not shown) of the instrument. Thus, when the upper and lower instrument jaws are shifted from an open to a closed position, the ram or driver 74 will shift downwardly to a staple forming position, from a normal retracted position. The pusher head 68 and compression spring 69 constantly urge the row of staples 67 forwardly, so that the forwardmost staple of the row passes through an opening in rear plate 72 and is located in slideway 73.

An angle plate 75 is affixed to the staple feed housing 66 and provides at the lower end of the slideway 73 an anvil 76 having an anvil surface 76a. When the ram or driver 74 is shifted downwardly by the closing of the instrument jaws, the driver will shift the forwardmost staple in slideway 73 downwardly until its crown engages anvil surface 76a. Further downward movement of driver 74 will form the staple about anvil 76.

To achieve the benefits of the teachings of the present invention in the operation of the surgical stapling instrument of U.S. Pat. No. 3,873,016, it is only necessary to provide the anvil 76 with an anvil surface 76a having a concave configuration similar to anvil surface 18a of FIG. 7. This is shown in FIG. 21. Under these circumstances, the driver 74 will be provided at its lower end with a notch and crown contacting edge equivalent to notch 45a and crown contacting edge 48a of FIG. 8. The operation of the thus modified anvil 76 and driver 74 will be the same as described with respect to FIGS. 9-11.

It will be understood that it would be within the scope of the invention to configure the anvil surface 76a of FIG. 21 after the manner of anvil surface 18b of FIG. 12 or anvil surface 18c of FIG. 14. Under these circumstances, the driver would be provided with a notch and crown contacting edge at its lower end configured like notch 45b and crown contacting edge 48b of FIG. 13 or notch 45c and crown contacting edge 48c of FIG. 15, respectively.

Figures 22, 23:
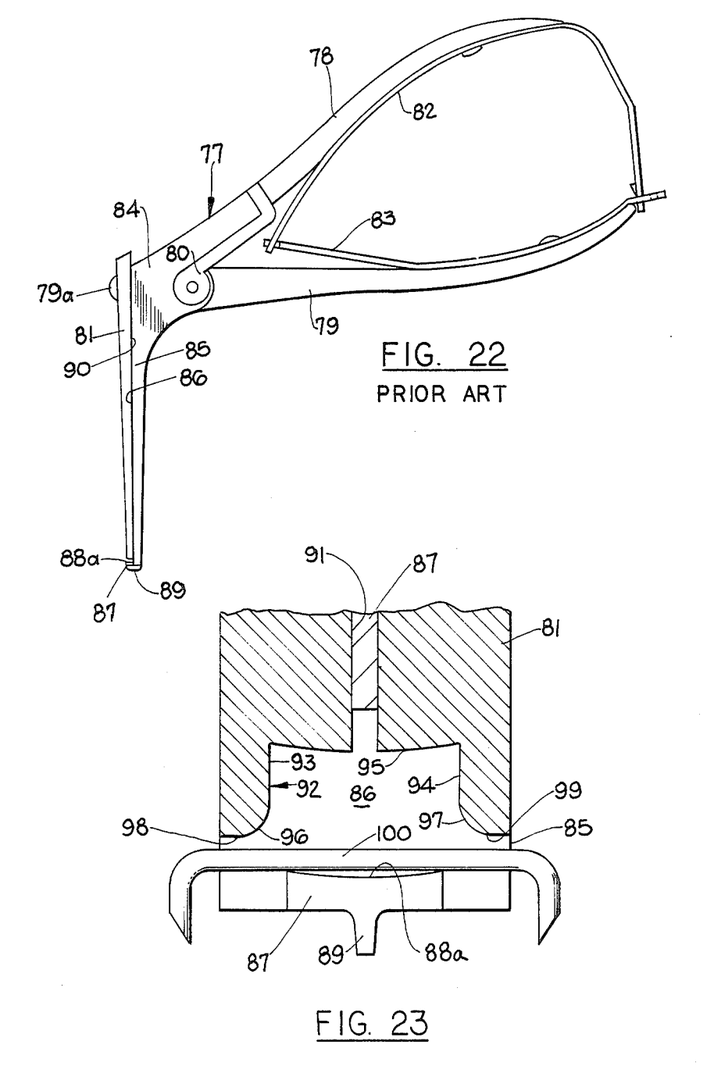
FIG. 22 is a side elevational view of yet another type of surgical skin stapler to which the teachings of the present invention are applicable.
FIG. 23 is a fragmentary, enlarged, front elevational view, partly in cross section, illustrating the anvil and driver of the instrument of FIG. 22 as modified in accordance with the teachings of the present invention.

The same sort of modification could be made to other types of skin staplers, such as that taught in U.S. Pat. No. 4,485,953. U.S. Pat. No. 4,485,953 describes a pliers-like surgical stapling instrument for use with a wholly separate one-piece cartridge containing a plurality of staples. Each staple is individually withdrawn from the cartridge by the surgical stapling instrument, to be implanted and formed in the skin of a patient. This surgical stapling instrument is illustrated in FIG. 22 and is generally indicated at 77. The surgical stapling instrument comprises a first or upper handle 78, a second or lower handle 79, a pivot pin and keeper assembly 80, a former 81, an upper spring 82 affixed to the upper handle 78 and a lower spring 83 affixed to the lower handle 79. The upper handle 78 has at its forward end a central body portion 84 terminating in an elongated downwardly depending nose portion 85. The central body portion 84 has a slot (not shown) formed therein. The forward end of lower handle 79 is located in this slot and is pivotally affixed therein by the pivot pin and keeper assembly 80.

The elongated nose portion 85 provides a flat forward face 86. Near its lower end the nose portion 85 is provided with a forwardly extending lug of T-shaped cross section, the shank portion of which is shown at 87 in FIG. 23. The nose portion 85 terminates in a forwardly extending anvil 87 having an anvil surface 88. The forwardly extending anvil 87 also has a downwardly depending flange or keel 89 which cooperates with the separate cartridge to properly align the bottom end of the nose portion 85 within the cartridge during pickup and removal therefrom of a surgical staple.

The former 81 of the surgical stapling instrument comprises an elongated member having a flat rear surface adapted to cooperate with the flat forward surface 86 of nose portion 85. Near its upper end, the former 81 has a slot or window (not shown) formed therethrough. The forwardmost end 79a of lower handle 79 extends through this slot and thereby engages the former 81. Just below the slot, the rear surface 90 of the former 81 is provided with a rearwardly extending lug of T-shaped cross section. This lug is adapted to be slidably received in appropriately configured slot means in the central body portion 84. Similarly, the lug of T-shaped cross section on the forward face of nose portion 85 is adapted to be received in an appropriately configured slot in former 81, a portion of which is shown at 91 in FIG. 23. In this way, former 81 is slidably and captively mounted on the forward surface 86 of nose portion 85 and is shiftable through the agency of lower handle 79 between a retracted position illustrated in FIG. 22 and a staple forming position.

In operation, the lower end of nose portion 85 including keel 89 is inserted in a longitudinal slot in the separate cartridge. The anvil 87 is located beneath the crown portion of a staple within the cartridge and the lower handle 79 is shifted toward the upper handle 78 until the staple crown in engaged between the anvil surface 88 and the lower end of former 81. Means are provided at the rearward ends of springs 82 and 83 to lock the handles in this position so that the as yet unformed staple can be withdrawn from the cartridge and located over the wound or incision site. Further closure of lower handle 79 toward upper handle 78 releases the springs 82 and 83 and causes the staple to be formed in substantially the same manner described with respect to FIGS. 3, 4 and 5A above. Upon release of the lower handle 79, the springs 82 and 83 cause it to return to its normal, unactuated position, returning the former 81 to its retracted position.

FIG. 23 illustrates the lower end of nose portion 85, the lower end of former 81, anvil 87 and keel 89 of the instrument of FIG. 22 with the anvil 87 and former 81 modified in accordance with the teachings of the present invention. To this end, the anvil surface 88a of anvil 87 is provided with a concave shape, as shown. Thus, the anvil surface 88a is similar to anvil surface 18a of FIGS. 7, 9 and 10.

The lower end of former 81 is provided with a notch generally indicated at 92. The notch 92 comprises a pair of parallel sides 93 and 94 joined by an arcuate, convex, staple crown-contacting surface 95. It will be noted that the parallel notch sides 93 and 94 terminate at their lower ends in gentle curves 96 and 97, which, in turn terminate in horizontal surfaces 98 and 99. Thus, the former notch 92 is similar to the notch 45a illustrated in FIG. 8. In FIG. 23, a surgical staple 100 is illustrated in position on anvil surface 88a. It will be understood by one skilled in the art that the forming of staple 100 will be substantially identical to that described in detail with respect to FIGS. 9, 10 and 11 with all of the advantages achieved by the practice of the present invention. It will further be understood that anvil surface 88a and the crown engaging edge 95 of the former could be configured as shown in FIGS. 12 and 13, respectively, or FIGS. 14 and 15, respectively.

In the description of the present invention presented above, the ideal shape of a surgical staple is shown and described with respect to FIG. 11 as being rectangular with leg portions 27 and 28 being substantially coaxial and leg tips 28 and 31 being substantially contiguous. At the present time, a surgical staple of this formed configuration is considered to be the industry standard. Should this standard change, or should other shapes be developed for specialized purposes, the teachings of the present invention can be employed to achieve controlled positioning and spacing of the leg tips and the particular desired angularity between leg portions 26 and 29 and the crown 25 utilizing a low force, with consistent results and without coining. By appropriate configuration of the anvil surface and the driver or former and its crown contacting edge, the final desired configuration of the staple can be achieved with compensation for the natural spring back properties of the material from which the staple is made.

It will be understood by one skilled in the art that words used herein such as "vertical", "horizontal", "upwardly", and "downwardly" are used in conjunction with the drawings for purposes of clarity. It will be appreciated that in use, a surgical stapling instrument can be held in any orientation required by the skin surface to which a staple is to be applied.

Modifications may be made in the invention without departing from the spirit of it. For example, throughout the above description, the crown portion of the surgical staple has been described as being rectilinear before and after forming. While this is generally the case, it is not a requirement for the practice of this invention. As an example, staples have been devised having crown portions with a raised central part for easier engagement by an extractor. The teachings of the present invention are equally applicable to such staples.

What we claim is:

1. An anvil and a driver for use with a surgical stapling instrument to form and implant a surgical staple of the type having a crown portion terminating at each end in a leg portion, said anvil being mounted on said instrument, said driver being shiftably supported by said instrument, said anvil having an anvil surface, said driver having a staple forming end, said driver being shiftable by said instrument between a normal retracted position and a staple forming position, said forming end of said driver having an inverted U-shaped notch therein adapted to receive said anvil when said driver is in said staple forming position, said notch being defined by side edges for bending the staple leg portions about said anvil at their junctures with said staple crown and a transverse edge joining said side edges and adapted to contact said staple crown during the staple forming operation, there being clearance between said side edges of said driver notch and said anvil greater than the transverse cross sectional dimension of said staple leg portions when said driver is in said staple forming position, said anvil surface being concave and said crown contacting driver edge being complimentary with and configured to cooperate therewith to impart a concave bow in said staple crown when said driver is in said forming position, said bow being of such dimension as to preclude plastic deformation of said crown, whereby more generous bends with less force and without coining and slight over-bending are achieved at the junctures of said staple leg portions and said staple crown and whereby when said driver is shifted from said staple forming position to said retracted position said crown returns to its initial state compensating for spring-back at said junctures of said leg portions and said crown portion, consistently producing the desired final formed configuration of said staple.

2. The anvil and driver claimed in claim 1 wherein said concave anvil surface is arcuate.

3. The anvil and driver claimed in claim 1 wherein said concave anvil surface is V-shaped.

4. The anvil and driver claimed in claim 1 wherein said concave anvil surface is faceted, comprising a plurality of adjacent surfaces.

5. The anvil and driver claimed in claim 1 wherein said crown contacting driver edge corresponds in shape to the shape of said anvil surface.

6. The anvil and driver claimed in claim 1 wherein said side edges of said driver notch are parallel.

7. The anvil and driver claimed in claim 1 wherein said crown engaging edge of said driver notch is interrupted by a second notch formed in said driver.

8. The anvil and driver claimed in claim 1 wherein said side edges of said driver notch terminate in outwardly curved edges at said forming end of said driver.

9. The anvil and driver claimed in claim 1 including at least one surgical staple, said surgical staple when fully formed by said anvil and said driver having a rectangular shape, said leg portions of said formed staple having opposed free ends substantially coaxially aligned and substantially contiguous.

10. The anvil and driver claimed in claim 1 including an anvil plate and a plurality of surgical staples arranged in a row in face-to-face relationship, each of said staple leg portions having a first part coaxial with said crown and a depending part terminating in a free end, said anvil plate comprising an elongated member having forward and rearward ends and being of inverted U-shaped cross section, said anvil plate having a longitudinally extending raised central planar portion, the longitudinal edges of which terminate in coextensive downwardly depending portions, each of said downwardly depending portions terminating in a flange portion extending laterally of said downwardly depending portion and said central portion, a coextensive extension on said central portion of said forward end of said anvil plate lying at a slight upward angle to said central portion, said extension comprising said anvil having said concave anvil surface, said flange portions extending the length of said anvil plate such that when said row of staples are mounted on said anvil plate straddling said raised central portion thereof, said free ends of said staples are supported by said flanges.

11. The anvil and driver claimed in claim 10 including coplanar extensions at the forward ends of said flanges such that when said staples of said row are mounted on said anvil plate straddling said raised central portion and said anvil, the free ends of all but the forwardmost staple of said row are supported by said flanges and said coplanar extensions.

12. A method of forming a surgical staple of the type having a crown portion terminating at its ends in leg portions, said method comprising the steps of providing an anvil having a concave anvil surface, providing a driver having a forming end, providing said driver forming end with an inverted U-shaped notch defined by side edges joined by a staple crown contacting edge configured to compliment and to cooperate with said concave anvil surface, sizing said notch such that said anvil can be received therein with clearance between said anvil and each of said notch sides greater than the transverse cross sectional dimensions of said staple leg portions, locating a staple on said anvil with the staple crown portion supported by said anvil surface, advancing said forming end of said driver toward said anvil, causing said notch sides to bend said staple at the junctures of said leg portions and said crown portion, engaging said staple crown portion between said crown contacting edge of said driver and said concave anvil surface to impart a temporary bow to said staple crown portion within the elastic limit of the material from which said staple is made, retracting said driver forming end from said anvil to free the formed staple from said driver and to permit said staple crown portion to return to its initial state compensating for natural spring back of said material from which said staple is made at said bends formed at the junctures of said staple leg portions and said crown portion.

13. The method claimed in claim 12 wherein said concave anvil surface is arcuate.

14. The method claimed in claim 12 wherein said concave anvil surface is V-shaped.

15. The method claimed in claim 12 wherein said concave anvil surface is faceted, comprising a plurality of adjacent surfaces.

* * * * *